(12) United States Patent
Ezaki et al.

(10) Patent No.: US 9,903,829 B2
(45) Date of Patent: Feb. 27, 2018

(54) BIOSENSOR AND MEASURING DEVICE USING SAME

(75) Inventors: Hirofumi Ezaki, Ehime (JP); Mamiko Ochi, Ehime (JP); Akihisa Higashihara, Ehime (JP); Eriko Yoshioka, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 14/111,301

(22) PCT Filed: Apr. 12, 2012

(86) PCT No.: PCT/JP2012/002522
§ 371 (c)(1),
(2), (4) Date: Oct. 11, 2013

(87) PCT Pub. No.: WO2012/140888
PCT Pub. Date: Oct. 18, 2012

(65) Prior Publication Data
US 2014/0037505 A1 Feb. 6, 2014

(30) Foreign Application Priority Data

Apr. 12, 2011 (JP) ................. 2011-087883
Apr. 12, 2011 (JP) ................. 2011-087885
Apr. 12, 2011 (JP) ................. 2011-087944

(51) Int. Cl.
*G01N 27/327* (2006.01)
*G01N 27/403* (2006.01)
(Continued)

(52) U.S. Cl.
CPC ........ *G01N 27/00* (2013.01); *B01L 3/502723* (2013.01); *B01L 3/502746* (2013.01);
(Continued)

(58) Field of Classification Search
CPC ................ G01N 27/00; G01N 27/3272; B01L 3/502746; B01L 3/502723;
(Continued)

(56) References Cited

U.S. PATENT DOCUMENTS 5,512,159 A * 4/1996 Yoshioka et al. ........ 204/403.08
6,591,852 B1 7/2003 McNeely et al.
(Continued)

FOREIGN PATENT DOCUMENTS

JP 11-344461 A 12/1999
JP 2002-181758 A 6/2002
(Continued)

OTHER PUBLICATIONS

International Search Report for PCT/JP2012/002522 dated Jul. 10, 2012.
(Continued)

*Primary Examiner* — Robert Eom
(74) *Attorney, Agent, or Firm* — Pearne & Gordon LLP

(57) ABSTRACT

Electrodes (A, B) are provided in at least one of plate-like members corresponding to an inner side direction of supply path from an opening of supply path. Electrode (C) of a biological sample is provided in the inner side direction from electrodes (A, B) Reagent part is provided so as to cover electrodes (A, B) and electrode (C). Inflow restricting hole of a sample liquid is provided in at least one of plate-like members corresponding to the portions on both sides of supply path closer to the opening side than the electrode.

8 Claims, 15 Drawing Sheets

(51) Int. Cl.
 *G01N 27/00* (2006.01)
 *B01L 3/00* (2006.01)
(52) U.S. Cl.
 CPC .. *G01N 27/3272* (2013.01); *B01L 2200/0684* (2013.01); *B01L 2300/0645* (2013.01); *B01L 2300/0825* (2013.01); *B01L 2300/14* (2013.01); *B01L 2400/0688* (2013.01); *B01L 2400/086* (2013.01)
(58) Field of Classification Search
 CPC ..... B01L 2200/0684; B01L 2300/0645; B01L 2300/0825; B01L 2300/14; B01L 2400/0688; B01L 2400/086
 USPC .................................. 422/50, 68.1, 81–82.04
 See application file for complete search history.

(56) References Cited

U.S. PATENT DOCUMENTS

| | | | |
|---|---|---|---|
| 6,645,359 | B1 | 11/2003 | Bhullar |
| 7,232,510 | B2 | 6/2007 | Miyazaki et al. |
| 7,850,839 | B2 | 12/2010 | Miyazaki et al. |
| 8,097,147 | B2 | 1/2012 | Miyazaki et al. |
| 8,101,063 | B2 | 1/2012 | Miyazaki et al. |
| 8,298,400 | B2 | 10/2012 | Miyazaki et al. |
| 2004/0067166 | A1 | 4/2004 | Karinka et al. |
| 2006/0228254 | A1 | 10/2006 | Kusaka et al. |
| 2007/0062262 | A1 | 3/2007 | Blaschke et al. |
| 2009/0120806 | A1 | 5/2009 | Onoda et al. |
| 2009/0148349 | A1 | 6/2009 | Guan et al. |

FOREIGN PATENT DOCUMENTS

| | | |
|---|---|---|
| JP | 2004-279150 A | 10/2004 |
| JP | 2006-509187 A | 3/2006 |
| JP | 2007-521498 A | 8/2007 |
| WO | 02/44705 A1 | 6/2002 |
| WO | 2007/026683 A1 | 3/2007 |

OTHER PUBLICATIONS

Office Action issued in corresponding Japanese Patent Application No. 2013-509797 dated Jun. 3, 2014.

Paul Vulto, et al., "Phaseguides: a paradigm shift in microfluidic priming and emptying", Lab On a Chip, vol. 11, No. 9, Jan. 1, 2011 (Jan. 1, 2011), p. 1596, XP055091039.

Supplementary European Search Report for Application No. 127712461-15542698629, dated Jul. 31, 2014.

* cited by examiner

BIOSENSOR AND MEASURING DEVICE USING SAME

TECHNICAL FIELD

The present invention relates to a biosensor which measures biological information, such as a blood glucose level, and a measuring device using the biosensor.

BACKGROUND ART

The configuration of a biosensor of the related art will be described.

The biosensor of the related art includes a first plate-like member and a second plate-like member which is provided on the first plate-like member through a spacer. In the spacer, an opening is formed on the outer circumferential surface of the first plate-like member or the second plate-like member. In the spacer, an supply path of a sample liquid which extends in an inner side direction of the first plate-like member or the second plate-like member from the opening is provided.

A detection electrode is provided at a position corresponding to the inner side direction from the opening of the supply path in at least one of the first plate-like member and the second plate-like member. An detecting electrode of the sample liquid is provided in the inner side direction from the detection electrode. A reagent part is provided so as to cover the detection electrode and the detecting electrode (for example, see PTL 1).

In the biosensor of the related art, an inflow-promoting hole of a sample liquid is provided at a position corresponding to the inner side of the detection electrode of the first plate-like member or the second plate-like member. With this configuration, the sample liquid is easily introduced into the supply path.

That is, the inflow-promoting hole is provided, such that a capillary action occurs in the supply path, and as a result, the sample liquid is smoothly introduced into the supply path. Since the detecting electrode is located on the inner side from the detection electrode, it can be detected that the sample liquid reliably reaches the reagent part.

If it is detected that the sample liquid reaches the detecting electrode, the reaction state of the reagent part by the sample liquid is detected by the detection electrode.

In the configuration biosensor of the related art described above, there is a problem in that the measurement result varies depending on a way of spotting the sample liquid in the opening of the supply path.

CITATION LIST

Patent Literature

PTL 1: PCT Japanese Translation Patent Publication No. 2007-521498

SUMMARY OF THE INVENTION

The invention has been accomplished in consideration of the above-described problem, and an object of the invention is to provide a biosensor and a measuring device using the same capable of suppressing variation in a measurement result depending on a way of spotting a sample liquid.

The invention provides a biosensor including a first plate-like member, and a second plate-like member provided on the first plate-like member through a spacer, in which, in the spacer, an opening is formed on the outer circumferential surface of the first or second plate-like member, and an supply path of a sample liquid which extends in an inner circumferential direction of the first or second plate-like member from the opening is provided. A detection electrode and a detecting electrode are provided on an inner side of the opening of the supply path, a reagent part is provided so as to cover the detection electrode and the detecting electrode, and an inflow-restricting part of the sample liquid is provided in at least one of the first and second plate-like members and the spacer on an inner side from the detection electrode in the portions on both sides of the supply path.

Since the inflow-restricting part is provided in the portions on both sides of the supply path, in the sample liquid in which the portions on both sides of the supply path go ahead, a capillary action is significantly suppressed in this portion. As a result, the sample liquid which enters toward the inner side of the supply path enters the inward portion of the supply path in a substantially horizontal state, thereby suppressing variation in the measurement result.

DESCRIPTION OF EMBODIMENTS

Figure 1:
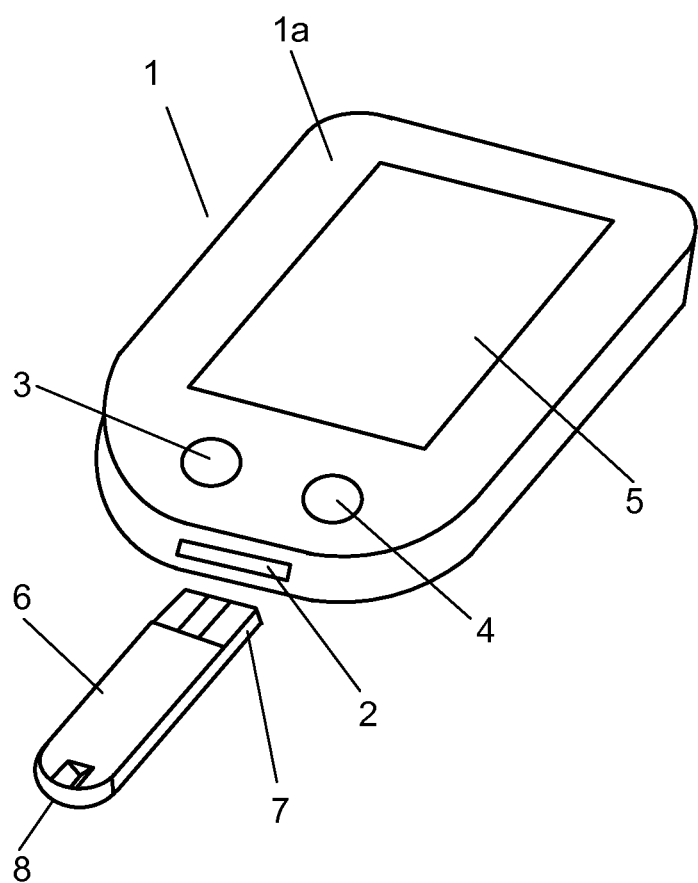
FIG. 1 is a perspective view of a measuring device using a biosensor according to a first embodiment of the invention.

Hereinafter, embodiments of the invention will be described referring to the drawings. It should be noted that the invention is not limited to the embodiments.

First Embodiment

First, a first embodiment of the invention will be described.

FIG. 1 is a perspective view showing the configuration of biosensor 6 and measuring device 1 according to the first embodiment of the invention.

Measuring device 1 has mounting part 2, into which biosensor 6 is inserted, at the leading end (in FIG. 1, a lower left side) of main body case 1a, and menu button 3, power button 4, and display unit 5 are provided on the upper surface of main body case 1a constituting measuring device 1. Biosensor 6 has insertion part 7 into mounting part 2 of main body case 1a constituting measuring device 1 on a rear end side (in FIG. 1, on an upper right side), and spotting part 8 of a sample liquid on a leading end side (in FIG. 1, a lower left side).

The configuration of biosensor 6 will be described.

Figure 2A:
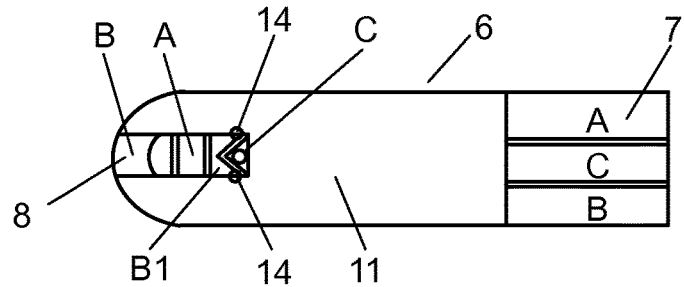
FIG. 2A is a partially cut plan view of the biosensor according to the first embodiment of the invention.
Figure 2B:
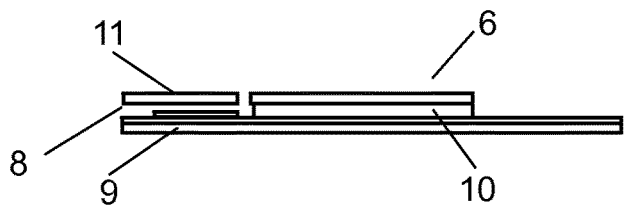
FIG. 2B is a side view of the biosensor according to the first embodiment of the invention.
Figure 2C:
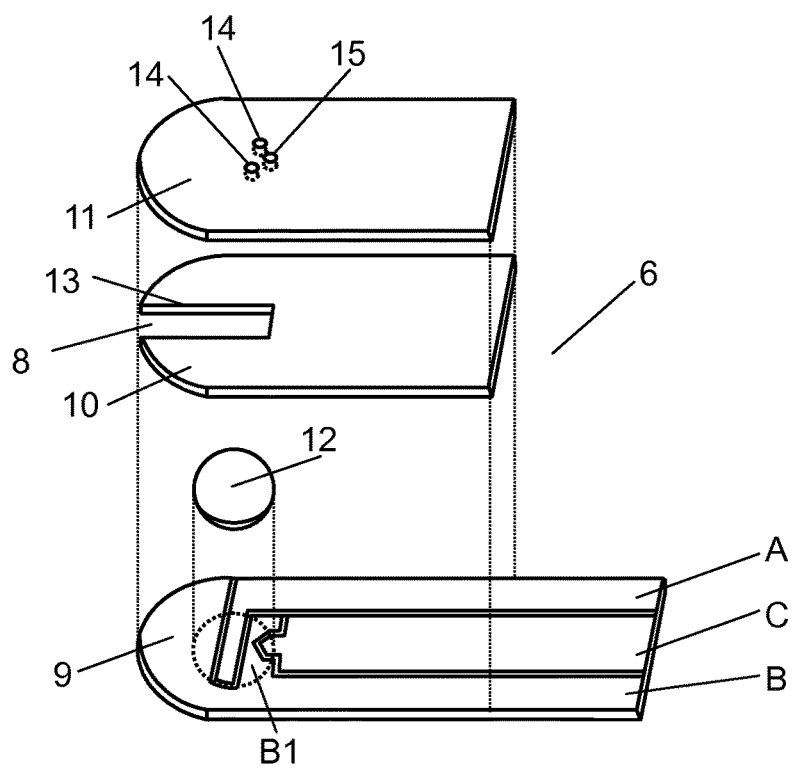
FIG. 2C is an exploded perspective view of the biosensor according to the first embodiment of the invention.

FIG. 2A is a partially cut plan view showing the configuration of biosensor 6 according to the first embodiment of the invention, FIG. 2B is a side view of biosensor 6 according to the first embodiment of the invention, and FIG. 2C is an exploded perspective view of biosensor 6 according to the first embodiment of the invention.

As shown in FIGS. 2A to 2C, biosensor 6 has a configuration in which elongated plate-like member 11 (also referring to as second plate-like member 11) is provided on elongated plate-like member 9 (also referred to as first plate-like member 9) through elongated plate-shaped spacer 10.

As shown in FIG. 2C, three electrodes A, B, and C are arranged in parallel in a longitudinal direction on plate-like member 9 in an insulating state.

On a leading end side (a left side of FIG. 2C) of three electrodes A, B, and C, first, electrode B extends in a direction perpendicular to the longitudinal direction, and next, electrode A extends in a direction perpendicular to the longitudinal direction on an inner side (a right side of FIG. 2C). Branched electrode B1 of electrode B extends in a direction perpendicular to the longitudinal direction, and next, electrode C is provided so as to extend in the longitudinal direction.

Circular reagent part 12 is provided so as to cover electrodes A, B, and C (see FIG. 2C).

In biosensor 6, electrode A and electrode B become detection electrodes. The characteristic of a sample liquid is detected on the basis of a current flowing between electrodes A and B and between electrodes A and B1.

In biosensor 6, electrode C becomes a detecting electrode. That is, it is detected whether or not the sample liquid reaches a predetermined position by a current flowing between electrodes A and C.

As shown in FIGS. 2A to 2C, in spacer 10, supply path 13 in which spotting part 8 side becomes an opening is provided from the opening toward the inner side (the right side of FIGS. 2A to 2C). The upper and lower surfaces of supply path 13 are covered with plate-like members 9 and 11. As shown in FIG. 2A, the rear end side (the right side of FIGS. 2A to 2C) of supply path 13 reaches the positions of electrode B, electrode A, branched electrode B1, and electrode C on the leading end side of biosensor 6.

Electrode (detecting electrode) C has a shape in which the central portion protrudes toward the opening of supply path 13 (see FIG. 3). Electrode A (working electrode) and electrode B (counter electrode) extend outside supply path 13 in a direction perpendicular to a direction from the opening of supply path 13 toward the inner side. Electrode C (detecting electrode) is arranged in an inner side direction from the opening of supply path 13.

Figure 3A:
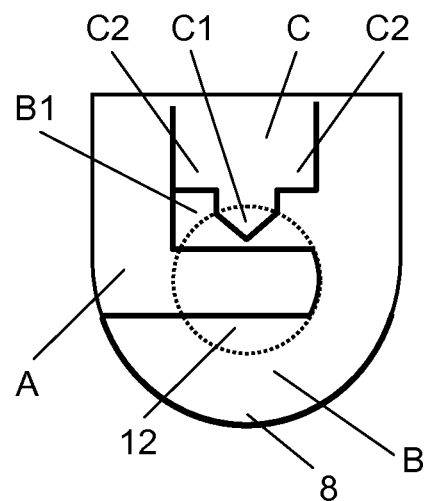
FIG. 3A is a diagram showing a main part of the biosensor according to the first embodiment of the invention.
Figure 3B:
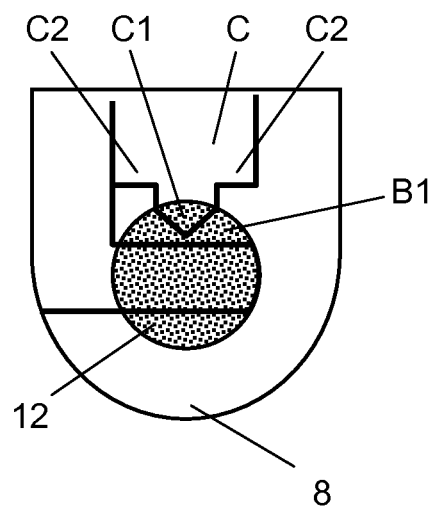
FIG. 3B is a diagram showing a main part of the biosensor according to the first embodiment of the invention.
Figure 3C:
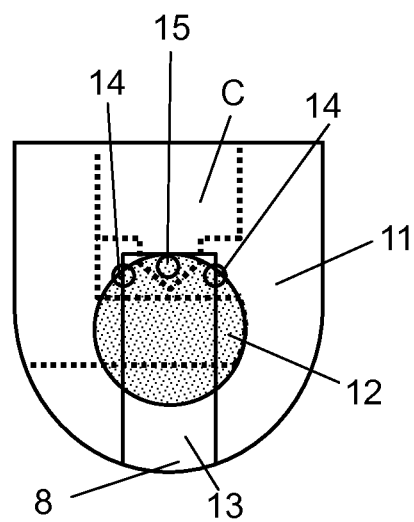
FIG. 3C is a diagram showing a main part of the biosensor according to the first embodiment of the invention.

The configuration of electrode C (detecting electrode) will be described in more detail. FIGS. 3A to 3C are main part plan views showing an electrode configuration of the biosensor according to the first embodiment of the invention. FIG. 3A shows an electrode configuration when no reagent part 12 is provided, FIG. 3B shows the relationship between reagent part 12 and an electrode configuration, and FIG. 3C shows the relationship between reagent part 12, supply path 13, and an electrode configuration.

As shown in FIGS. 3A to 3C, a central portion of electrode C (detecting electrode) having the horizontal width of supply path 13 protrudes toward spotting part 8 (in FIG. 3A, a lower side) to form protrusion C1. In a normal state, if the sample liquid is spotted in spotting part 8, the sample liquid reaches protrusion C1 of electrode C (detecting electrode) through electrode B (counter electrode), electrode A (working electrode), and branched electrode B1 (counter electrode). That is, the sample liquid flows sequentially from the leading end side of reagent part 12 toward the rear end side.

Both sides of protrusion C1 of electrode C (detecting electrode) are arranged behind central protrusion C1 (the upper side in FIG. 3A), and become rear parts C2.

Rear parts C2 on both sides of electrode (detecting electrode) C are arranged behind protrusion C1 outside supply path 13 (see FIG. 3C). With this configuration, even if the sample liquid flows ahead on both sides of supply path 13, at this time, it is possible to prevent branched electrode B1 of electrode B (counter electrode) and electrode C (detecting electrode) from being in a conduction state through rear parts C2.

This point will be described in more detail. As described above, when the sample liquid flows ahead on both sides of supply path 13, the progression of the sample liquid in the central portion of supply path 13 is delayed. Accordingly, although a reaction in reagent part 12 is delayed, branched electrode B1 of electrode B (counter electrode) and electrode C (detecting electrode) are in a conduction state through rear parts C2, it is not possible to make an appropriate measurement. Therefore, in this embodiment, in order to avoid this program, rear parts C2 of electrode C (detecting electrode) are arranged outside supply path 13.

In conformity with the shape of electrode C (detecting electrode), a portion of branched electrode B1 facing protrusion C1 has a shape recessed from an inner side toward a front side, and conversely, portions facing rear parts C2 have a shape protruding from the front side toward the inner side (see FIG. 3A).

With this configuration, the sample liquid reaching electrode C (detecting electrode) can be detected in a portion between protrusion C1 and electrode A (working electrode). In this portion, when reaching of the sample liquid is detected, the sample liquid in which both sides of supply path 13 flow ahead reaches reagent part 12 on branched electrode B1 (counter electrode). Accordingly, it is possible to appropriately detect the sample liquid flowing in reagent part 12.

In biosensor 6 of this embodiment, as shown in FIG. 2A, a pair of inflow-restricting holes 14 of the sample liquid are provided in plate-like member 11 on the inner side of electrode A (working electrode) in the portions on both sides of supply path 13.

In this embodiment, as described above, inflow-restricting holes 14 of the sample liquid are provided on the inner side of electrode A (working electrode). As shown in FIG. 3C, a pair of inflow-restricting holes 14 are provided so as to be located on both sides of protrusion C1 of electrode C (detecting electrode).

Inflow-restricting holes 14 are provided so as to face the upper surface of reagent part 12.

In plate-like member 11, an inflow-promoting hole 15 of the sample liquid is provided at a position in the inner side direction from inflow-restricting holes 14 and in the inner side direction from protrusion C1 in the central portion of supply path 13.

Although an example where a pair of inflow-restricting holes 14 and inflow-promoting hole 15 are provided in plate-like member 11, the invention is not limited to this example, inflow-restricting holes 14 and inflow-promoting hole 15 may be provided in at least one of plate-like members 9 and 11.

A pair of inflow-restricting holes 14 are punched from the side of plate-like member 9 or 11 opposite to spacer 10 toward spacer 10. Punching includes punching by press molding and boring by laser. In this way, inflow-restricting holes 14 of this embodiment formed punching by press molding or boring by laser have a circular shape.

Figure 4:
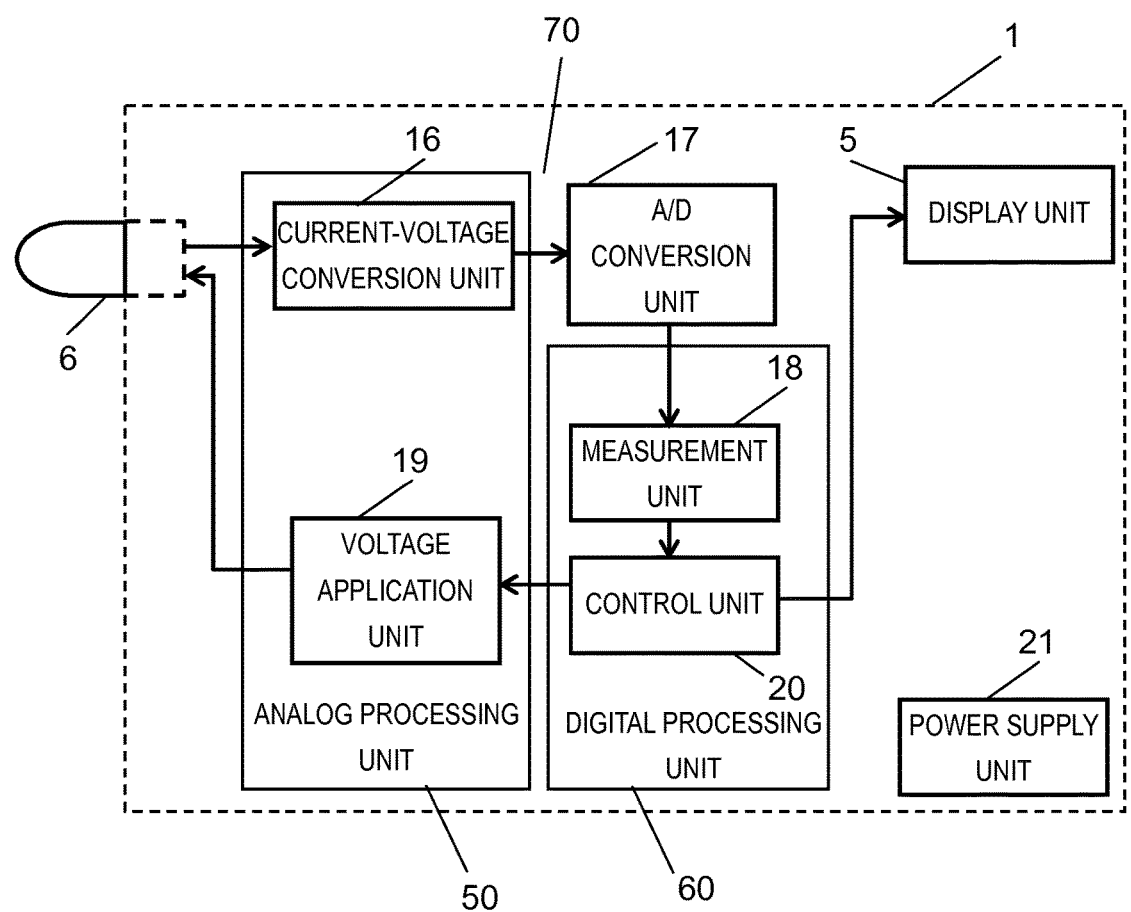
FIG. 4 is a circuit block diagram of a measuring device according to the first embodiment of the invention.

FIG. 4 is a circuit block diagram of measuring device 1 according to the first embodiment of the invention. Measuring device 1 has analog processing unit 50 having current-voltage conversion unit 16 and voltage application unit 19. Measuring device 1 has digital processing unit 60 having determination unit 18 and control unit 20. Measuring device 1 has A/D conversion unit 17, display unit 5, and power supply unit 21. Measuring device 1 has measurement unit 70 having analog processing unit 50, digital processing unit 60, and A/D conversion unit 17.

A measurement result of biosensor 6 is processed by determination unit 18 through current-voltage conversion unit 16 and A/D conversion unit 17. The measurement result is displayed on display unit 5 through control unit 20.

For the measurement, a voltage is applied from voltage application unit 19 to electrodes A, B, and C and branched electrode B1.

Figure 5A:
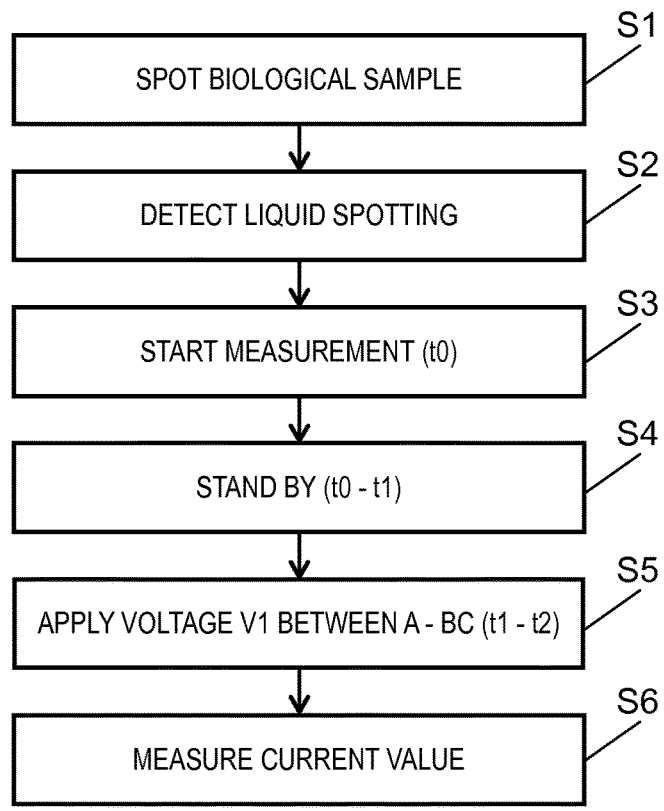
FIG. 5A is a flowchart showing blood glucose level measurement processing of the measuring device according to the first embodiment of the invention.
Figure 5B:
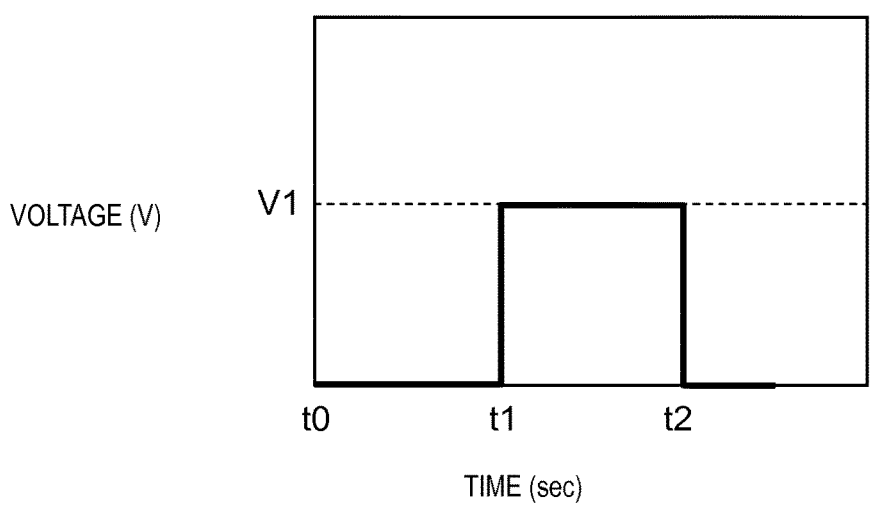
FIG. 5B is a diagram showing a voltage to be applied to electrodes by a voltage application unit of the measuring device according to the first embodiment of the invention.

For example, a case where a blood glucose level is measured using measuring device 1 having the above configuration will be described. FIG. 5A is a flowchart showing blood glucose level measurement processing of measuring device 1 according to the first embodiment of the invention, and FIG. 5B is a diagram showing a voltage to be applied to electrodes A, B, and C and branched electrode B1 by voltage application unit 19 of measuring device 1 according to the first embodiment of the invention. FIGS. 6A to 6E are diagrams showing an entering state of a sample liquid of the biosensor according to the first embodiment of the invention.

Figure 6A:
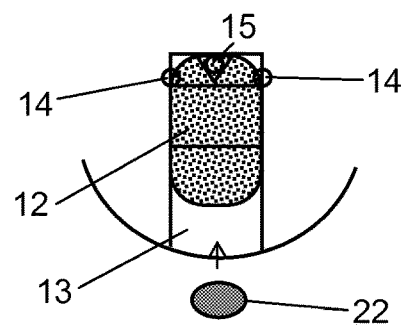
FIG. 6A is a diagram showing an entering state of a sample liquid of the biosensor according to the first embodiment of the invention.

As shown in FIG. 4, a user puts biosensor 6 in measuring device 1, and in this state, blood 22 which is an example of the sample liquid is spotted in spotting part 8 (see S1 of FIG. 5A and FIG. 6A).

Figure 6B:
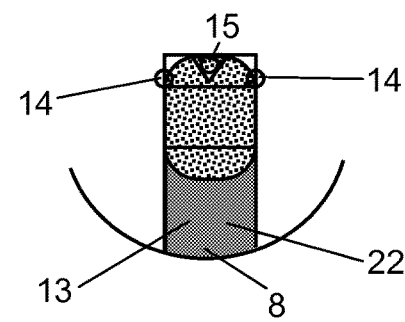
FIG. 6B is a diagram showing an entering state of a sample liquid of the biosensor according to the first embodiment of the invention.
Figure 6C:
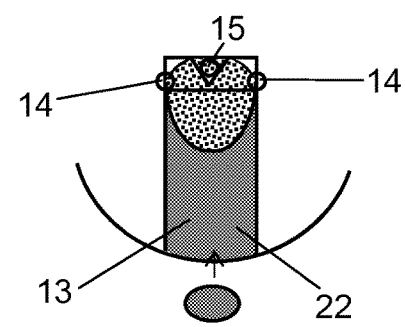
FIG. 6C is a diagram showing an entering state of a sample liquid of the biosensor according to the first embodiment of the invention.

Then, as shown in FIGS. 6B and 6C, blood 22 enters toward the inner side of supply path 13 by a capillary action.

The capillary action between plate-like members 9 and 11 in supply path 13 appears when a gap between plate-like members 9 and 11 is small. In order that blood 22 smoothly enters toward the inner side of supply path 13 by the capillary action, in this embodiment, a surfactant is coated on the lower surface (supply path 13 side) of plate-like member 11.

At this time, as shown in FIG. 6C, there is a case where the portions on both sides of supply path 13 enters toward the inner side of supply path 13 ahead of the central portion depending on a way of spotting blood 22.

In this embodiment, the progression of blood 22 entering toward the inner side of supply path 13 in the portions on both sides of supply path 13 ahead of the central portion of supply path 13 can be suppressed by inflow-restricting holes 14.

Figure 6D:
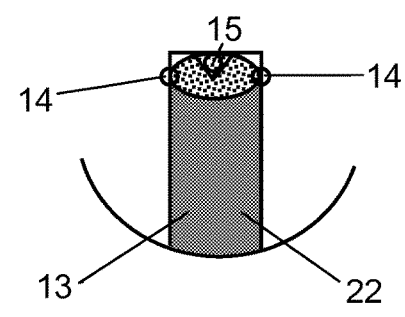
FIG. 6D is a diagram showing an entering state of a sample liquid of the biosensor according to the first embodiment of the invention.

As a result, the entering of blood 22 in the central portion of supply path 13 progresses as shown in FIG. 6D, eventually, the central portion is substantially horizontally aligned with the portions on both sides, and finally, as shown in FIG.

Figure 6E:
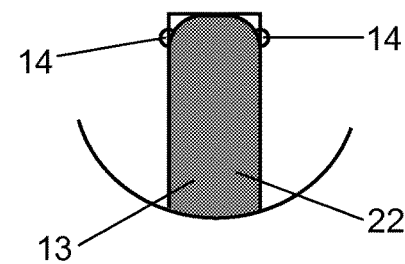
FIG. 6E is a diagram showing an entering state of a sample liquid of the biosensor according to the first embodiment of the invention.

6E, blood 22 enters toward the inner side of supply path 13 (if blood 22 is appropriately spotted in spotting part 8, as shown in FIG. 6E, the central portion of blood 22 progresses toward the inner side ahead of both sides).

In the entering state of blood 22 in supply path 13 shown in FIGS. 6A to 6E, as will be understood from FIGS. 3A to 3C, blood 22 reaching between electrodes A and B is detected when blood 22 enters and a current flows between electrodes A and B with a reaction of reagent part 12.

If blood 22 further enters toward the inner side of supply path 13, a current flow between electrodes A and C (protrusion C1). Accordingly, blood 22 reaching the inner side of supply path 13, that is, blood 22 reaching the entire surface of reagent part 12 is detected (S2 of FIG. 5A).

When the detection time is t0 of FIG. 5B (S3 of FIG. 5A), a measurement starts. From this, it stands by for a predetermined reaction time (t0 to t1) of reagent part 12 (S4 of FIG. 5A). Thereafter, a voltage V1 is applied between electrodes A-B (including branched electrode B1) and between electrodes A-C (S5 of FIG. 5A) based on electrode A. The blood glucose level is measured on the basis of a current value obtained at this time by determination unit 18 of FIG. 4 (S6 of FIG. 5A), and displayed on display unit 5 (a technique for detecting the blood glucose level is disclosed in, for example, Pamphlet of International Publication No. 2002/44705).

As described above, in this embodiment, inflow-restricting holes 14 of the sample liquid are provided in at least one of plate-like members 9 and 11 corresponding to the portions on both sides of supply path 13 on the inner side of electrode A (working electrode).

Accordingly, in a state where the portions on both sides of supply path 13 go ahead of the central portion depending on a way of spotting the sample liquid, even though the sample liquid enters electrodes B (counter electrode) and A (working electrode), branched electrode B1, and electrode C (detecting electrode), it is possible to suppress the preceding entering state of the sample liquid in the portions on both sides of supply path 13.

Specifically, since inflow-restricting holes 14 are provided in the portions on both sides of supply path 13, in the sample liquid in which the portions on both sides of supply path 13 go ahead, the capillary action is significantly suppressed in the portions of inflow-restricting holes 14. Since inflow-restricting holes 14 are present, the surfactant on the lower surface of plate-like member 11 is removed in the portions of inflow-restricting holes 14 on both sides of supply path 13. As a result, as shown in FIG. 6E, the sample liquid which enters toward the inner side of supply path 13 enters the inward portion of supply path 13 in a substantially horizontal state, thereby suppressing variation in the measurement result.

In this way, as shown in FIG. 6E, in order that the sample liquid which enters toward the inner side of supply path 13 enters the inward portion of supply path 13 in a substantially horizontal state, inflow-restricting holes 14 are arranged to face each other in the portions on both sides of supply path 13.

In contrast, if inflow-restricting holes 14 are not provided in the portions on both sides of supply path 13, the sample liquid which enters the portions on both sides of supply path 13 ahead reaches electrode C (detecting electrode) only through a portion near the outer circumference of reagent part 12 shown in FIG. 3C, and in this state (the amount of the sample liquid entering the central portion of reagent part 12 is balanced), a subsequent detection process starts, resulting in variation in the measurement result.

In this embodiment, as described above, inflow-restricting holes 14 are provided in the portions on both sides of supply path 13, such that the capillary action by the sample liquid entering the portions on both sides of supply path 13 ahead is significantly suppressed in this portion. As a result, the sample liquid which enters toward the inner side of supply path 13 enters the inward portion of supply path 13 in a substantially horizontal state, thereby suppressing variation in the measurement result.

In the biosensor of this embodiment, since inflow-restricting holes 14 are provided to face reagent part 12, from this point, it is possible to increase the inflow suppression effect by inflow-restricting holes 14.

Specifically, although the sample liquid in which the portions on both sides of supply path 13 go ahead temporarily stops to enter toward the inner side in the portions of inflow-restricting holes 14, the sample liquid may go toward electrode C (detecting electrode) again through the outer circumference of inflow-restricting holes 14.

However, in this embodiment, since inflow-restricting holes 14 are provided to face reagent part 12, a force is applied to allow blood 22 toward the electrode (detecting electrode) again through the outer circumference of inflow-restricting holes 14 to penetrate in reagent part 12 present in that portion. From this, the amount around inflow-restricting holes 14 going toward electrode C (detecting electrode) is significantly restrained, and from this point, it is possible to increase the inflow suppression effect by inflow-restricting holes 14.

Second Embodiment

A measuring device according to a second embodiment of the invention has the same structure and functions as the measuring device according to the first embodiment of the invention, and thus description thereof will not be repeated.

The biosensor according to the second embodiment of the invention is different from the biosensor according to the first embodiment of the invention, and will be thus described referring to the drawings. However, the same configurations as the biosensor of the first embodiment are represented by the same reference numerals, and description thereof will not be repeated.

As shown in FIGS. 7A to 7D, biosensor 26 of the second embodiment has a configuration in which elongated plate-like member 11 (also referred to as second plate-like member 11) is provided on elongated plate-like member 9 (also referred to as first plate-like member 9) through elongated plate-shaped spacer 10.

Figure 7A:
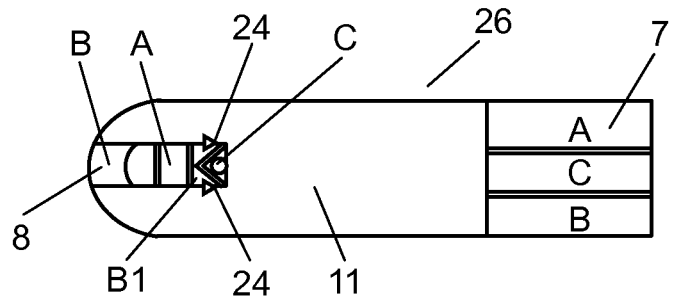
FIG. 7A is a partially cut plan view of a biosensor according to a second embodiment of the invention.
Figure 7B:
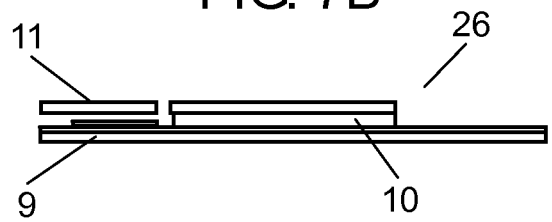
FIG. 7B is a side view of the biosensor according to the second embodiment of the invention.
Figure 7C:
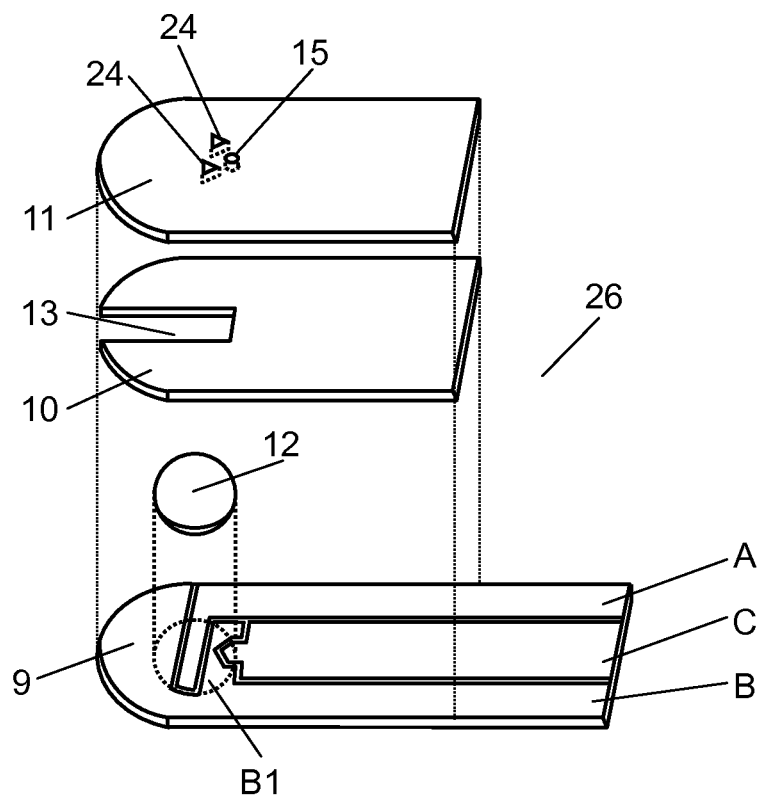
FIG. 7C is an exploded perspective view of the biosensor according to the second embodiment of the invention.

This embodiment has a feature in that, as shown in FIGS. 7A, and 7C, a pair of triangular inflow-restricting holes 24 of a sample liquid are provided in plate-like member 11 on the inner side of electrode (working electrode) A in the portions on both sides of supply path 13.

Figure 7D:
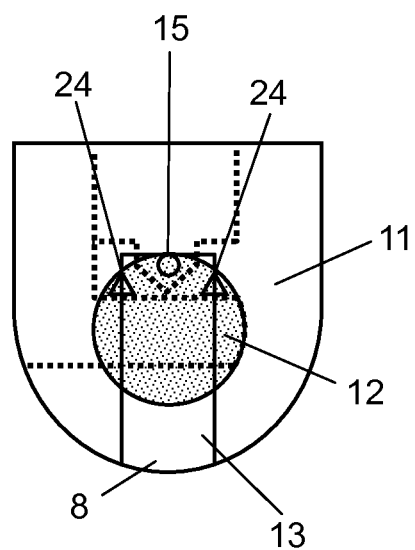
FIG. 7D is a diagram showing a main part of the biosensor according to the second embodiment of the invention.

In this embodiment, inflow-restricting holes 24 of the sample liquid are provided on the inner side of electrode (working electrode) A, and as shown in FIGS. 7A and 7D, are provided on both sides of protrusion C1 of electrode C (detecting electrode).

Inflow-restricting holes 24 are provided to face the upper surface of reagent part 12.

In the central portion of supply path 13, inflow-promoting hole 15 of the sample liquid is provided in plate-like member 11 in the inner side direction from inflow-restricting holes 24 and in the inner side direction from protrusion C1.

Although inflow-restricting holes 24 and inflow-promoting hole 15 are provided in plate-like member 11, inflow-restricting holes 24 and inflow-promoting hole 15 may be provided in at least one of plate-like members 9 and 11.

Inflow-restricting holes 24 are punched from the side of plate-like member 9 or 11 opposite to spacer 10 toward spacer 10. Punching includes punching by press molding and boring by laser.

Figure 8A:
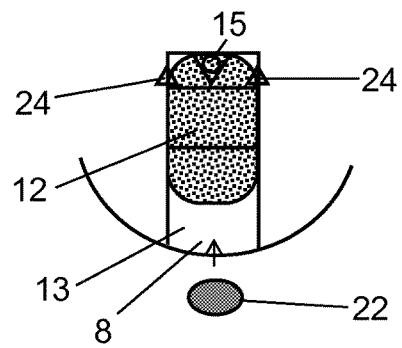
FIG. 8A is a diagram showing an entering state of a sample liquid of the biosensor according to the second embodiment of the invention.

In the above configuration, for example, when measuring the blood glucose level, as shown in FIG. 8A, blood (an example of the sample liquid) 22 is spotted in spotting part 8.

Figure 8B:
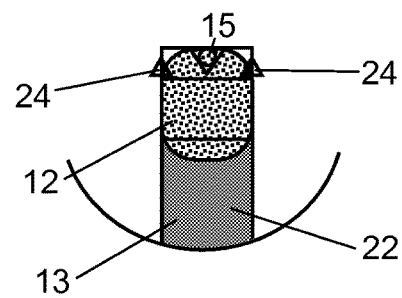
FIG. 8B is a diagram showing an entering state of a sample liquid of the biosensor according to the second embodiment of the invention.
Figure 8C:
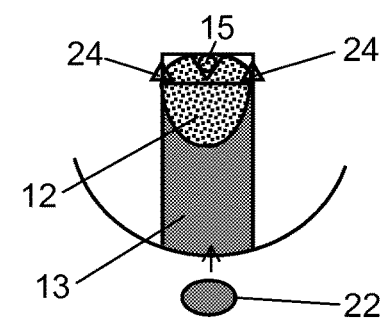
FIG. 8C is a diagram showing an entering state of a sample liquid of the biosensor according to the second embodiment of the invention.

When this happens, as shown in FIGS. 8B and 8C, blood 22 enters toward the inner side of supply path 13 by the capillary action. At this time, as shown in FIG. 8C, the portions on both sides of supply path 13 enter toward the inner side of supply path 13 ahead of the central portion depending on a way of spotting blood 22.

In this embodiment, the progression of blood 22 entering toward the inner side of supply path 13 in the portions on both sides of supply path 13 ahead of the central portion of supply path 13 can be suppressed by inflow-restricting holes 24.

Figure 8D:
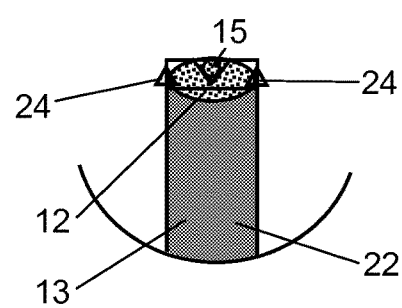
FIG. 8D is a diagram showing an entering state of a sample liquid of the biosensor according to the second embodiment of the invention.
Figure 8E:
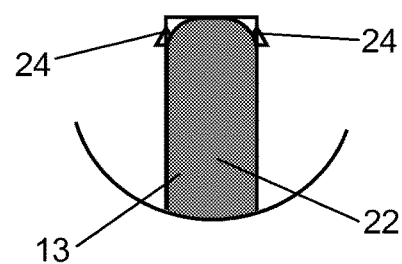
FIG. 8E is a diagram showing an entering state of a sample liquid of the biosensor according to the second embodiment of the invention.

As a result, as shown in FIG. 8D, eventually, the central portion is substantially horizontally aligned with the portions on both sides, and finally, as shown in FIG. 8E, blood 22 enters toward the inner side of supply path 13. If blood 22 is appropriately spotted in spotting part 8, as shown in FIG. 8E, the central portion of blood 22 progresses toward the inner side ahead of both sides.

As shown in FIG. 8E, in order that the sample liquid which enters toward the inner side of supply path 13 enters the inward portion of supply path 13 in a substantially horizontal state, inflow-restricting holes 24 are arranged to face each other in the portions on both sides of supply path 13.

As described above, inflow-restricting holes 24 of this embodiment have a base which has a triangular shape perpendicular to the portions on both sides of supply path 13. For this reason, since the base portions of triangular inflow-restricting holes 24 are perpendicular to the progression direction of the sample liquid which enters the portions on both sides of supply path 13 ahead, the action to suppress the entering of the sample liquid increases. As a result, it is possible to more effectively suppress variation in the measurement result depending on a way of spotting the sample liquid.

In this embodiment, since inflow-restricting holes 24 are provided to face reagent part 12, from this point, it is possible to increase the inflow suppression effect by inflow-restricting holes 24.

Specifically, although the sample liquid in which the portions on both sides of supply path 13 go ahead temporarily stops to enter toward the inner side in the portions of inflow-restricting holes 24, the sample liquid may go toward electrode C (detecting electrode) again through the outer circumference of inflow-restricting holes 24.

However, in this embodiment, inflow-restricting holes 24 are provided to face reagent part 12. For this reason, a force is applied to allow blood 22 as one of the sample liquid toward the electrode C (detecting electrode) again through the outer circumference of inflow-restricting holes 24 to penetrate in reagent part 12 present in that portion. From this, blood 22 around inflow-restricting holes 24 going toward electrode C (detecting electrode) is significantly restrained, and from this point, it is possible to increase the inflow suppression effect by inflow-restricting holes 24.

Third Embodiment

Figure 9:
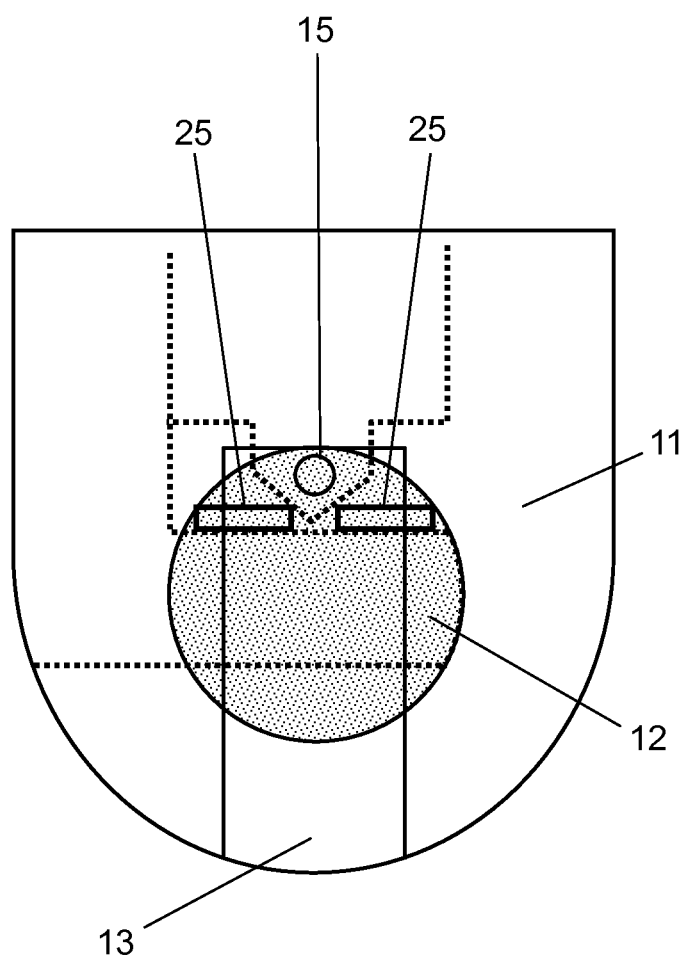
FIG. 9 is a diagram showing a main part of a biosensor according to a third embodiment of the invention.

As a third embodiment of the invention, as shown in FIG. 9, inflow-restricting holes 25 have a quadrangular shape. In the quadrangular shape of the inflow-restricting holes 25, since a base portion is perpendicular to the progression direction of the sample liquid which enters the portions on both sides of supply path 13 ahead, it is possible to obtain the same inflow suppression effect as when inflow-restricting holes 24 have a triangular shape.

Fourth Embodiment

A measuring device according to a fourth embodiment of the invention has the same structure and functions as the measuring device according to the first embodiment of the invention and the second embodiment of the invention, and thus description thereof will not be repeated.

A biosensor according to the fourth embodiment of the invention is different from the biosensor according to the first embodiment of the invention and the second embodiment of the invention, and will be thus described referring to the drawings. However, the same configurations as the biosensor of the first embodiment or the second embodiment are represented by the same reference numerals, and thus description thereof will not be repeated.

As shown in FIGS. 10A to 10D, biosensor 36 of the fourth embodiment has a configuration in which elongated plate-like member 11 (also referred to as second plate-like member 11) is provided on elongated plate-like member 9 (also referred to as first plate-like member 9) through elongated plate-shaped spacer 10.

Figure 10A:
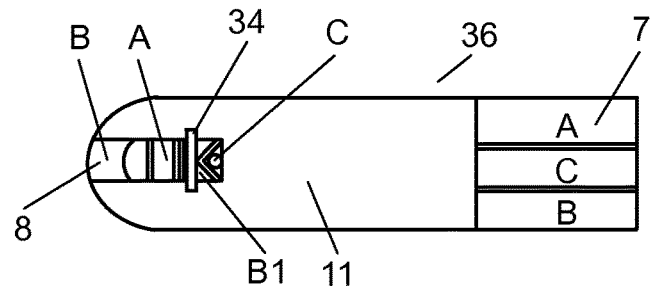
FIG. 10A is a partially cut plan view of a biosensor according to a fourth embodiment of the invention.
Figure 10B:
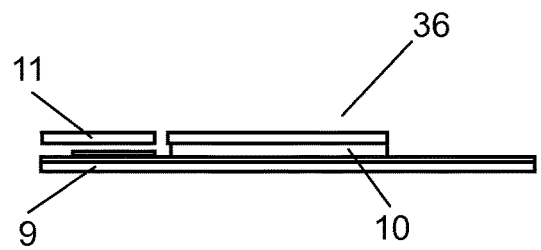
FIG. 10B is a side view of the biosensor according to the fourth embodiment of the invention.
Figure 10C:
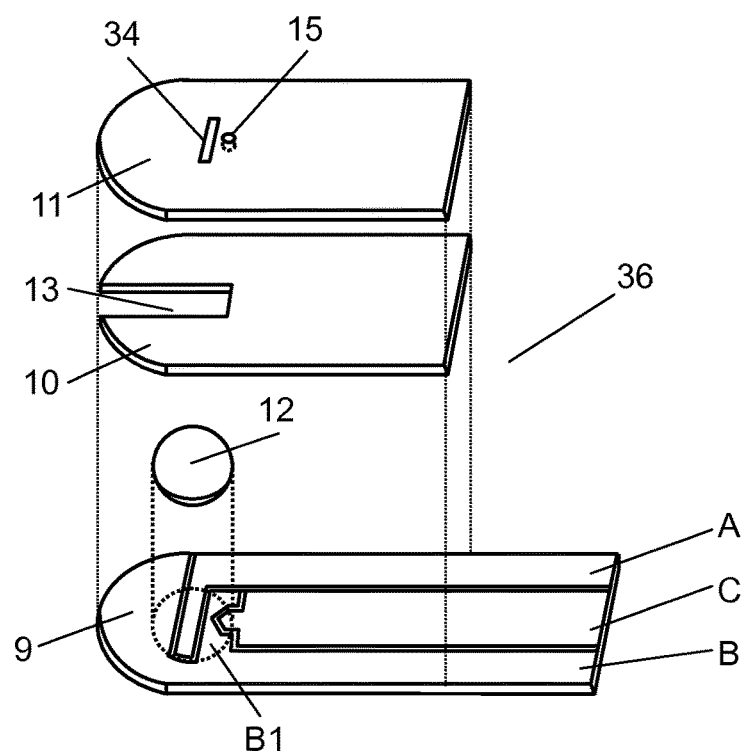
FIG. 10C is an exploded perspective view of the biosensor according to the fourth embodiment of the invention.
Figure 10D:
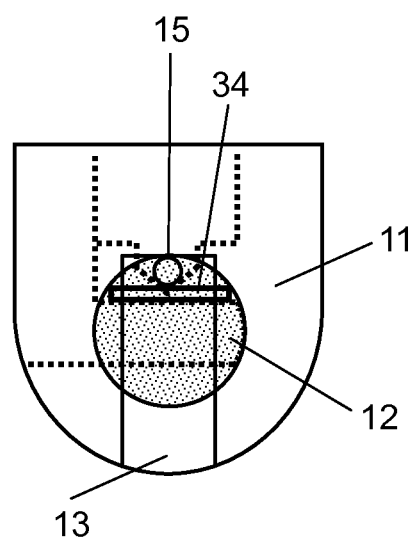
FIG. 10D is a diagram showing a main part of the biosensor according to the fourth embodiment of the invention.

This embodiment has a feature in that, as shown in FIGS. 10A and 10D, inflow-restricting hole 34 of a sample liquid is provided to have a width greater than supply path 13 over both sides of supply path 13 in plate-like member 11 on the inner side of electrode A (working electrode).

In this embodiment, inflow-restricting hole 34 of the sample liquid is provided on the inner side of electrode A (working electrode), and as shown in FIGS. 10A and 10D, one inflow-restricting hole 34 is provided so as to span both sides of protrusion C1 of electrode C (detecting electrode).

Inflow-restricting hole 34 is provided to face the upper surface of reagent part 12.

In the central portion of supply path 13, inflow-promoting hole 15 of the sample liquid is provided in plate-like member 11 in the inner side direction from inflow-restricting hole 34 and in the inner side direction from protrusion C1.

Although inflow-restricting hole 34 and inflow-promoting hole 15 are provided in plate-like member 11, inflow-restricting hole 34 and inflow-promoting hole 15 may be provided in at least one of plate-like members 9 and 11.

Inflow-restricting hole 34 is punched from the side of plate-like member 9 or 11 opposite to spacer 10 toward spacer 10. Punching includes punching by press molding and boring by laser.

Inflow-restricting hole 34 of this embodiment has a rectangular shape which is continuously provided from one of both sides of supply path 13 to the other side.

Specifically, as shown in FIGS. 10A and 10D, the base which is continuous from one of both sides of supply path 13 to the other side has a grooved rectangular shape which is perpendicular to the opening side of supply path 13.

Figure 11A:
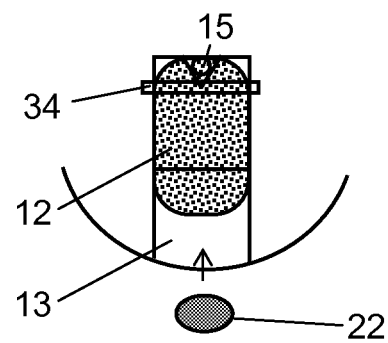
FIG. 11A is a diagram showing an entering state of a sample liquid of the biosensor according to the fourth embodiment of the invention.

In the above configuration, for example, when measuring the blood glucose level, as shown in FIG. 11A, blood 22 which is an example of the sample liquid is spotted in spotting part 8.

Figure 11B:
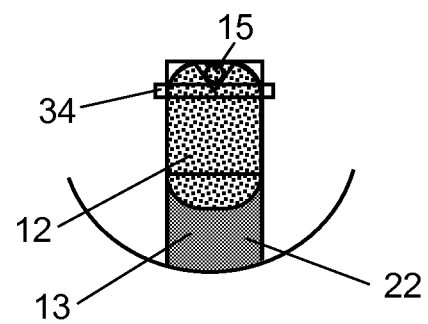
FIG. 11B is a diagram showing an entering state of a sample liquid of the biosensor according to the fourth embodiment of the invention.
Figure 11C:
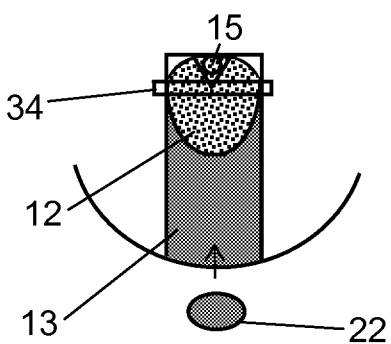
FIG. 11C is a diagram showing an entering state of a sample liquid of the biosensor according to the fourth embodiment of the invention.

Then, as shown in FIGS. 11B and 11C, blood 22 enters toward the inner side of supply path 13 by a capillary action.

At this time, as shown in FIG. 11C, the portions on both sides of supply path 13 enter toward the inner side of supply path 13 ahead of the central portion depending on a way of spotting blood 22.

In this embodiment, the progression of blood 22 entering toward the inner side of supply path 13 in the portions on both sides of supply path 13 ahead of the central portion of supply path 13 can be suppressed by inflow-restricting hole 34.

Figure 11D:
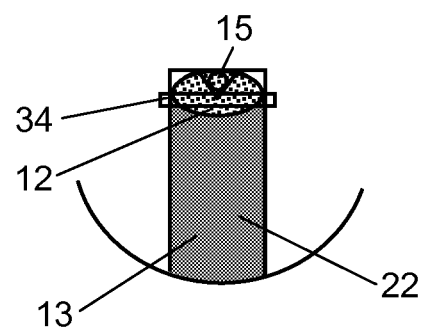
FIG. 11D is a diagram showing an entering state of a sample liquid of the biosensor according to the fourth embodiment of the invention.
Figure 11E:
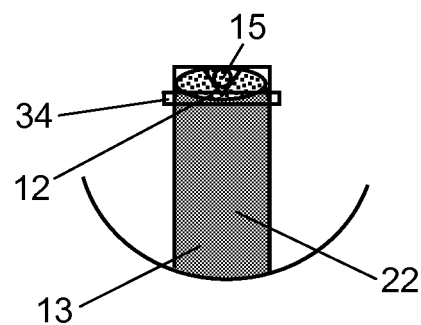
FIG. 11E is a diagram showing an entering state of a sample liquid of the biosensor according to the fourth embodiment of the invention.

As a result, as shown in FIG. 11D, eventually, the central portion is substantially horizontally aligned, and as shown in FIG. 11E, finally enters toward the inner side of supply path 13. If blood 22 is appropriately spotted in spotting part 8, as shown in FIG. 11F, the central portion of blood 22 progresses toward the inner side ahead of both sides.

Figure 11F:
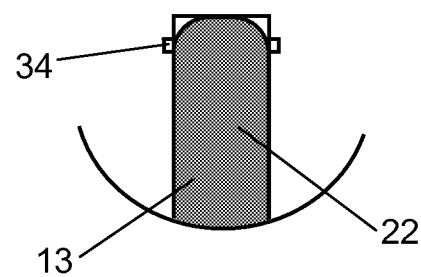
FIG. 11F is a diagram showing an entering state of a sample liquid of the biosensor according to the fourth embodiment of the invention.

As shown in FIGS. 11E and 11F, in order that the sample liquid which enters toward the inner side of supply path 13 enters the inward portion of the supply path 13 in a substantially horizontal state, inflow-restricting hole 34 is arranged so as to connect the opposing portions on both sides of supply path 13.

Inflow-restricting hole 34 of this embodiment is continuously provided from one of both sides of supply path 13 to the other side. For this reason, since inflow-restricting hole 34 is perpendicular to the progression direction of the sample liquid which enters the portions on both sides of supply path 13 ahead, the action to suppress the entering of the sample liquid increases, and as a result, it is possible to more effectively suppress variation in the measurement result depending on a way of spotting the sample liquid.

In this embodiment, since inflow-restricting hole 34 is provided to face reagent part 12, from this point, it is possible to increase the inflow suppression effect by inflow-restricting hole 34.

Specifically, the sample liquid in which the portions on both sides of supply path 13 go ahead temporarily stops to enter toward the inner side in the portion of inflow-restricting hole 34.

In this embodiment, since inflow-restricting hole 34 is provided to face reagent part 12, a force is applied to allow blood 22 temporarily stopped to enter toward the inner side to penetrate in reagent part 12 in this portion. From this, blood 22 going toward electrode C (detecting electrode) is significantly restrained, and from this point, it is possible to increase the inflow suppression effect by inflow-restricting hole 34.

Fifth Embodiment

Figure 12:
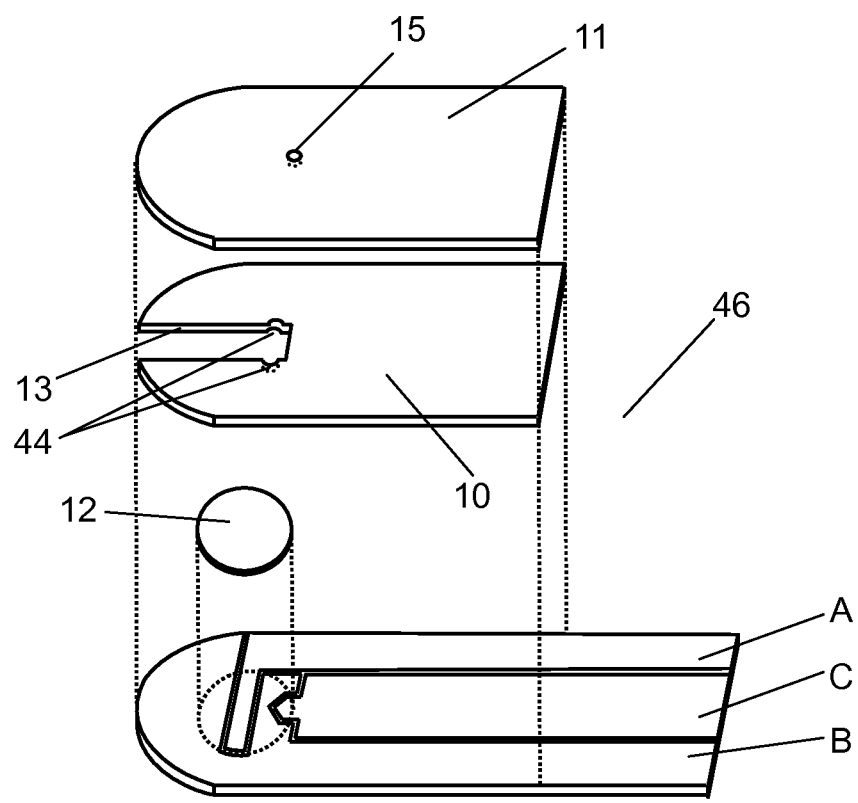
FIG. 12 is an exploded perspective view of a biosensor according to a fifth embodiment of the invention.

FIG. 12 shows biosensor 46 according to a fifth embodiment of the invention. In biosensor 46 according to the fifth embodiment of the invention, inflow-restricting concave parts 44 are provided as an inflow-restricting part of a sample liquid.

That is, inflow-restricting concave parts 44 are recessed outward of supply path 13.

Specifically, as shown in FIG. 12, inflow-restricting concave parts 44 are formed in spacer 10 like supply path 13, and have a semicircular shape recessed outward of supply path 13.

There is a case where, in a state where the portions on both sides of supply path 13 go ahead, the sample liquid enters electrodes B (counter electrode) and A (working electrode), branched electrode B1, and electrode C (detecting electrode) depending on a way of spotting sample liquid in biosensor 46. As shown in FIG. 12, inflow-restricting concave parts 44 are provided as an inflow-restricting part of a sample liquid, thereby suppressing the preceding entering state of the portions on both sides.

Specifically, when the sample liquid in which the portions on both sides of supply path 13 go ahead reaches inflow-restricting concave parts 44, a method of entering outward of supply path 13 is changed, and the sample liquid is collected in inflow-restricting concave parts 44 in the changed portion.

That is, the progression of the sample liquid in which the portions on both sides of supply path 13 go ahead is suppressed by inflow-restricting concave parts 44, and as a result, the sample liquid which enters toward the inner side of supply path 13 enters the inward portion of supply path 13 in a horizontal state, thereby suppressing variation in the measurement result.

As described above, the invention provides a biosensor including a first plate-like member, and a second plate-like member provided on the first plate-like member through a spacer, in which, in the space, an opening is formed on the outer circumferential surface of the first or second plate-like member, an supply path of a sample liquid which extends in an inner circumferential direction of the first or second plate-like member from the opening is provided, a detection electrode and a detecting electrode are provided on an inner side of the opening of the supply path, a reagent part is provided so as to cover the detection electrode and the detecting electrode, and an inflow-restricting hole of the sample liquid is provided in at least one of the first and second plate-like members corresponding to an inner side from the detection electrode in the portions on both sides of the supply path. For this reason, it is possible to suppress variation in the measurement result depending on a way of spotting the sample liquid.

That is, in the invention, the inflow-restricting hole of the sample liquid is provided in at least one of the first and second plate-like members corresponding to the inner side from the detection electrode in the portions on both sides of the supply path. With this configuration, in a state where the portions on both sides of the supply path go ahead depending on a way of spotting the sample liquid, even though the sample liquid enters the detection electrode and the detecting electrode, it is possible to suppress the preceding entering state.

Specifically, since the inflow-restricting hole is provided in the portions on both sides of the supply path, in the sample liquid in which the portions on both sides of the supply path go ahead, the capillary action is significantly suppressed in this portion, and as a result, the sample liquid which enters toward the inner side of the supply path enters the inward portion of the supply path in a horizontal state, thereby suppressing variation in the measurement result.

INDUSTRIAL APPLICABILITY

According to the invention, for example, the utilization as a biosensor which measures biological information, such as a blood glucose level, and a measuring device using the biosensor is expected.

REFERENCE MARKS IN THE DRAWINGS

1: measuring device
1a: main body case
2: mounting part
3: menu button
4: power button
5: display unit 6, 26, 36, 46: biosensor
7: insertion part
8: spotting part
9: plate-like member
10: spacer
11: plate-like member
12: reagent part
13: supply path
14, 24, 25, 34: inflow-restricting hole
15: inflow-promoting hole
16: current-voltage conversion unit
17: A/D conversion unit
18: determination unit
19: voltage application unit
20: control unit
21: power supply unit
22: blood
44: inflow-restricting concave part
70: measurement unit
A: working electrode (second detection electrode)
B: counter electrode (first detection electrode)
B1: branched electrode
C: electrode (detecting electrode)
C1: protrusion
C2: rear part

The invention claimed is:

1. A biosensor comprising:
a first plate-like member;
a spacer provided on the first plate-like member, the spacer having an opening formed as a cutout extending from an outer circumferential edge of the spacer to an inner portion of the spacer;
a second plate-like member provided on the spacer;
a supply path for supplying a sample liquid in the opening from the outer circumferential edge toward the inner portion of the spacer;
a working electrode at an outer circumferential edge side of the opening, a detecting electrode on an inner portion side of the opening, and a counter electrode between the working electrode and the detecting electrode; and
a reagent part on the working electrode, the counter electrode, and the detecting electrode,
wherein two inflow-restricting holes for restricting flow of the sample liquid are provided in the second plate-like member over the counter electrode provided between the working electrode and the detecting electrode, along both sides of the supply path, and corresponding to the portions on both sides of supply path, and
an inflow-promoting hole for promoting flow of the sample liquid is provided in the first or second plate-like member over the detecting electrode and at the inner portion side of the opening relative to the two inflow-restricting holes.

2. The biosensor of claim 1, wherein the two inflow-restricting holes triangular shaped and oriented such that a base of the triangular shape is perpendicular to the supply path.

3. The biosensor of claim 1, wherein the two inflow-restricting holes are rectangular and extend across a width of the supply path.

4. The biosensor of claim 1, wherein the two inflow-restricting holes are provided to face an upper surface of the reagent part.

5. A measuring device comprising:
a main body case having a mounting part, in which the biosensor of claim 1 is mounted;
a measurement unit connected to the mounting part of the main body case and to the biosensor; and
a display unit connected to the measurement unit.

6. A measuring device comprising:
a main body case having a mounting part, in which the biosensor of claim 2 is mounted;
a measurement unit connected to the mounting part of the main body case and to the biosensor; and
a display unit connected to the measurement unit.

7. A measuring device comprising:
a main body case having a mounting part, in which the biosensor of claim 3 is mounted;
a measurement unit connected to the mounting part of the main body case and to the biosensor; and
a display unit connected to the measurement unit.

8. A measuring device comprising:
a main body case having a mounting part, in which the biosensor of claim 4 is mounted;
a measurement unit connected to the mounting part of the main body case and to the biosensor; and
a display unit connected to the measurement unit.

* * * * *